US011219381B2

(12) United States Patent
Chen

(10) Patent No.: US 11,219,381 B2
(45) Date of Patent: Jan. 11, 2022

(54) NURSING BED BASED ON HEART RATE MONITORING AND VOICE RECOGNITION

(71) Applicant: Xue Chen, Guangdong (CN)

(72) Inventor: Xue Chen, Guangdong (CN)

( * ) Notice: Subject to any disclaimer, the term of this patent is extended or adjusted under 35 U.S.C. 154(b) by 29 days.

(21) Appl. No.: 16/197,395

(22) Filed: Nov. 21, 2018

(65) Prior Publication Data

US 2020/0113458 A1    Apr. 16, 2020

(30) Foreign Application Priority Data

Oct. 16, 2018   (CN) .......................... 201811202076.7
Oct. 16, 2018   (CN) .......................... 201821673628.8

(51) Int. Cl.
| | |
|---|---|
| *A61B 5/024* | (2006.01) |
| *A61G 7/002* | (2006.01) |
| *A61B 5/00* | (2006.01) |
| *A61G 7/018* | (2006.01) |
| *A61B 5/11* | (2006.01) |

(52) U.S. Cl.
CPC ...... *A61B 5/02405* (2013.01); *A61B 5/02444* (2013.01); *A61B 5/6891* (2013.01); *A61B 5/6892* (2013.01); *A61G 7/018* (2013.01); *A61B 5/1115* (2013.01); *A61G 2203/10* (2013.01)

(58) Field of Classification Search
CPC . A61B 5/6891; A61B 5/02405; A61B 5/1115; A61G 7/018
See application file for complete search history.

(56) References Cited

U.S. PATENT DOCUMENTS

| | | | | |
|---|---|---|---|---|
| 10,610,115 | B1* | 4/2020 | Zapesochny | A61B 5/0402 |
| 2010/0318026 | A1* | 12/2010 | Grunwald | A61B 5/742 |
| | | | | 604/95.05 |
| 2011/0301440 | A1* | 12/2011 | Riley | G06F 19/00 |
| | | | | 600/301 |
| 2015/0022330 | A1* | 1/2015 | Collins, Jr | A61B 5/1115 |
| | | | | 340/286.07 |
| 2015/0164721 | A1* | 6/2015 | Miyashita | A61G 7/0573 |
| | | | | 5/617 |
| 2017/0067774 | A1* | 3/2017 | Gough | A61G 7/0527 |
| 2017/0202463 | A1* | 7/2017 | Muhlsteff | A61B 5/0002 |
| 2017/0281017 | A1* | 10/2017 | Halperin | A61B 5/7275 |
| 2018/0099116 | A1* | 4/2018 | Ashby | A61B 5/11 |

(Continued)

OTHER PUBLICATIONS

Gubner, Richard S., et al. "Ballistocardiography." Circulation, vol. 7, No. 2, 1953, pp. 268-286. (Year: 1953).*

(Continued)

*Primary Examiner* — Allen Porter
*Assistant Examiner* — Adreanne A. Arnold

(57) ABSTRACT

Provided is a nursing bed based on heart rate monitoring and voice recognition. The nursing bed includes a nursing bed body, a drive motor and a controller. The nursing bed body includes a bed body fixed part, a bed body movable part and a connector. The bed body fixed part is hinged with a side of the connector, and the bed body moveable part is connected with another side of the connector fixedly. A motor base of the drive motor is installed on the bed body fixed part fixedly, an output shaft of the drive motor is connected with another part of the connector in a meshing manner, and the drive motor is configured to drive the bed body moveable part to swing through the connector.

5 Claims, 4 Drawing Sheets

(56) References Cited

U.S. PATENT DOCUMENTS

2018/0338725 A1* 11/2018 Shan .................... A47C 31/008
2020/0113458 A1* 4/2020 Chen ..................... A61B 5/318

OTHER PUBLICATIONS

Eblen-Zajjur, Antonio. "A Simple Ballistocardiographic System for a Medical Cardiovascular Physiology Course." Advances in Physiology Education, vol. 27, No. 4, 2003, pp. 224-229. (Year: 2003).*
Giovangrandi, L., et al. "Ballistocardiography—A Method Worth Revisiting." 2011 Annual International Conference of the IEEE Engineering in Medicine and Biology Society, 2011 (Year: 2011).*

* cited by examiner

NURSING BED BASED ON HEART RATE MONITORING AND VOICE RECOGNITION

CROSS REFERENCE TO RELATED APPLICATIONS

The present application claims the benefit of Chinese Patent Application Nos. 201811202076.7 and 201821673628.8 both filed on Oct. 16, 2018. All the above are hereby incorporated by reference.

TECHNICAL FIELD

The application relates to the field of electromechanical technologies, in particular to a nursing bed based on heart rate monitoring and voice recognition.

BACKGROUND

With increasing anticipated life span of the human beings, an aging society is getting closer and closer to us, and is accompanied by heavy burdens of the society and families as a result of senile diseases. How to improve the living quality of a senile patient and relieve economic and living pressures of the society and the families is the first question that the society must face at present. An elder dependency rate is one of indexes of measuring the burden of the aging society. At present, many inconveniences are found when the senile patient uses an electric nursing bed and need to be improved urgently, so as to fit the needs of a convalescent and improve the living quality and self-help ability. An electric switch is required by the existing electric nursing bed to control an angle of a bed board of the electric nursing bed. It is difficult for part of old people to operate the electric switch due to arm or leg inconvenience. The existing electric nursing bed lacks intelligentization. A risen backrest bed board needs to be adjusted back to a flat and straight state manually, and the backrest bed board with a certain angle may influence the sleep quality when the old people fall asleep. When adjusting the angles of the backrest bed boards for part of old people having weak vital signs or heart diseases, the health of old people may be influenced if the backrest bed board of the electric nursing bed is adjusted quickly or slowly.

SUMMARY

The present invention provides a nursing bed based on heart rate monitoring and voice recognition, to solve the problem in the conventional art that an angle of a backrest bed board of the existing nursing bed needs to be controlled manually and is difficult to be adjusted automatically in accordance with a vital sign or a sleep state of a user.

The specific technical solution is as follows:

A nursing bed based on heart rate monitoring and voice recognition includes a nursing bed body, a drive motor and a controller.

The nursing bed body includes a bed body fixed part, a bed body movable part and a connector. The bed body fixed part is hinged with a side of the connector, and the bed body moveable part is connected with another side of the connector fixedly.

A motor base of the drive motor is installed on the bed body fixed part fixedly; an output shaft of the drive motor is connected with another part of the connector in a meshing manner; and the drive motor is configured to drive the bed body moveable part to swing through the connector.

The controller is installed on the nursing bed body and electrically connected with the drive motor. The controller includes a motor drive module, an MCU module and a voice recognition module. The voice recognition module is configured to acquire voice information of a user and send the voice information to the MCU module. The MCU module is configured to analyze the voice information that is received and generate a control instruction of controlling the motor drive module. The motor drive module is configured to receive the control instruction of the MCU module, and accordingly control operations of the drive motor.

The nursing bed based on heart rate monitoring and voice recognition further includes a heart rate testing mattress. The heart rate testing mattress includes a mattress main body and a heart rate signal acquisition device. The controller further includes a heart rate signal processing module. The heart rate signal acquisition device is arranged under the mattress main body and configured to acquire a vibration signal of the mattress and transmit the vibration signal to the heart rate signal processing module. The heart rate signal processing module is configured to sample, quantify and filter the vibration signal, so as to acquire a heart rate vibration signal, and transmit the heart rate vibration signal to the MCU module.

The MCU module is further configured to analyze the heart rate vibration signal that is received, to accordingly analyze a sleep state and/or a health state of a person on the heart rate testing mattress.

Further, the voice recognition module includes a voice recorder and a voice processor. The voice processor includes a voice recognition instruction library unit, a voice input unit, an analysis morpheme unit and an instruction reference unit. The voice recorder is configured to record and generate voice information.

The voice input unit is configured to pre-process the voice information generated by the voice recorder. The analysis morpheme unit is configured to store the voice information after pre-processing and analyze various morpheme information or character strings. The instruction reference unit pairs various morpheme information or strings with word reference, then generating the control instruction, and then sending the control instruction to the MCU module.

Further, the voice recorder includes a microphone, a noise reduction device and a voice chip, which are connected sequentially.

The voice chip is connected with the voice processor. The voice chip is configured to implement digital-to-analog conversion for voice that is received and generate the voice information. The noise reduction device is configured to implement noise reduction for the voice information received from the microphone.

Further, the controller further includes a communication module. The communication module is configured to communicate with the Internet or a wireless network outside the nursing bed based on heart rate monitoring and voice recognition.

Further, the nursing bed based on heart rate monitoring and voice recognition further includes a monitoring module. The monitoring module is installed on the bed body fixed part or the bed body moveable part and configured to acquire video data and transmit the video data to the communication module.

Further, the nursing bed based on heart rate monitoring and voice recognition further includes a positioning module. The positioning module is configured to acquire positioning information of the nursing bed based on heart rate monitoring and voice recognition and transmit the positioning information to the communication module.

Further, the nursing bed based on heart rate monitoring and voice recognition further includes a vital sign sensor. The vital sign sensor is arranged on the bed body fixed part or the bed body moveable part and configured to acquire physiological characteristic data of the user and transmit the physiological characteristic data to the communication module.

Further, the nursing bed based on heart rate monitoring and voice recognition further includes a voice output module. The voice output module is arranged on the bed body fixed part or the bed body moveable part and configured to acquire voice data and transmit the voice data to the communication module.

Further, the nursing bed based on heart rate monitoring and voice recognition further includes an image acquisition device. The image acquisition device is arranged on the bed body fixed part or the bed body moveable part and configured to acquire image data or video data and transmit the image data or video data to the communication module.

With the adoption of the nursing bed based on heart rate monitoring and voice recognition provided by the present invention, the voice information of the user can be acquired, and the voice information may form the control instruction of controlling the drive motor. Then the controller may interpret the sleep state and health state of the user in accordance with a heart rate of a user while automatically controlling the nursing bed based on heart rate monitoring and voice recognition in accordance with the sleep state to restore the flat state and controlling a speed of the drive motor in accordance with the health state. With the adoption of the present invention, voice control is implemented for the drive motor which changes an angle of a bed board of the nursing bed based on heart rate monitoring and voice recognition, and the operations and speed of the drive motor are automatically controlled in accordance with the heart rate of the user. In this way, the nursing bed based on heart rate monitoring and voice recognition is more intelligentized and humane.

DETAILED DESCRIPTION OF THE EMBODIMENTS

Figure 1:
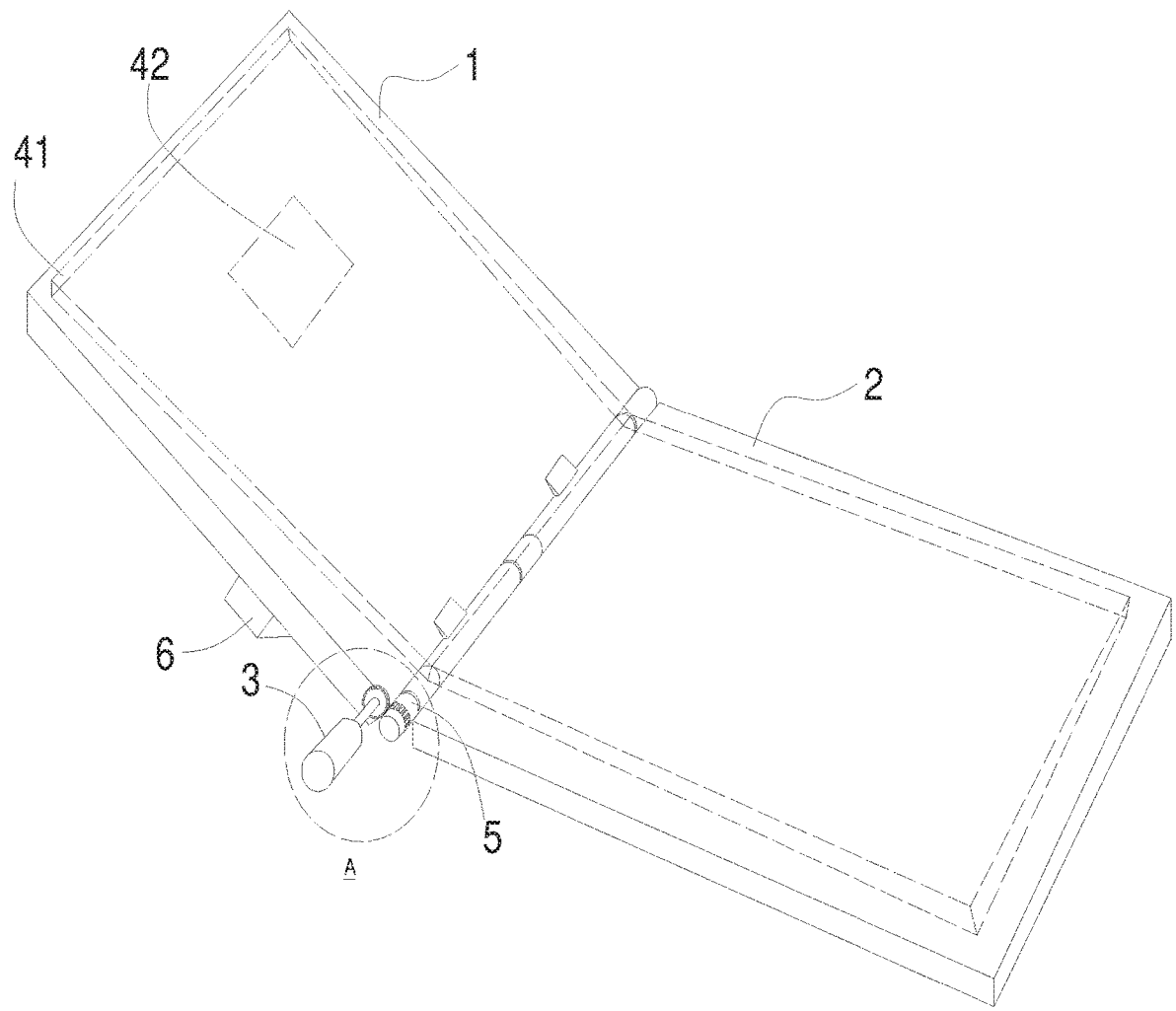
FIG. 1 is a structure diagram of a nursing bed based on heart rate monitoring and voice recognition in an embodiment of the present invention.
Figure 2:
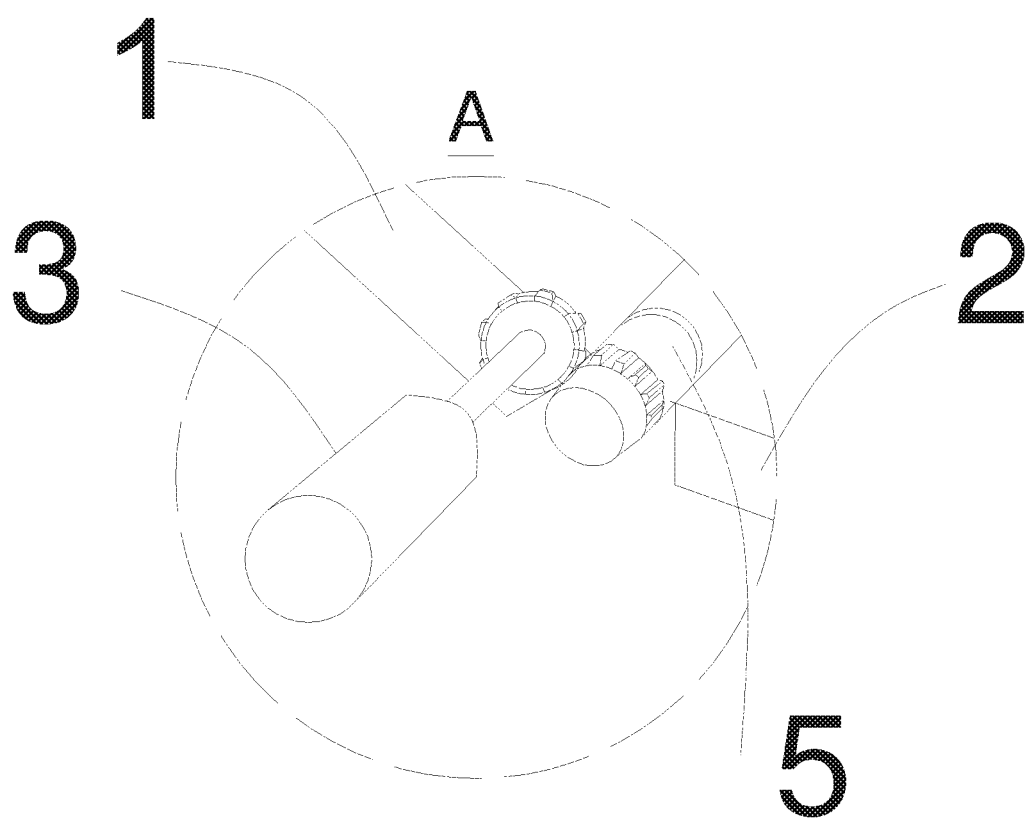
FIG. 2 is a partially enlarged drawing of a visual direction A of FIG. 1 in description of the present invention.
Figure 3:
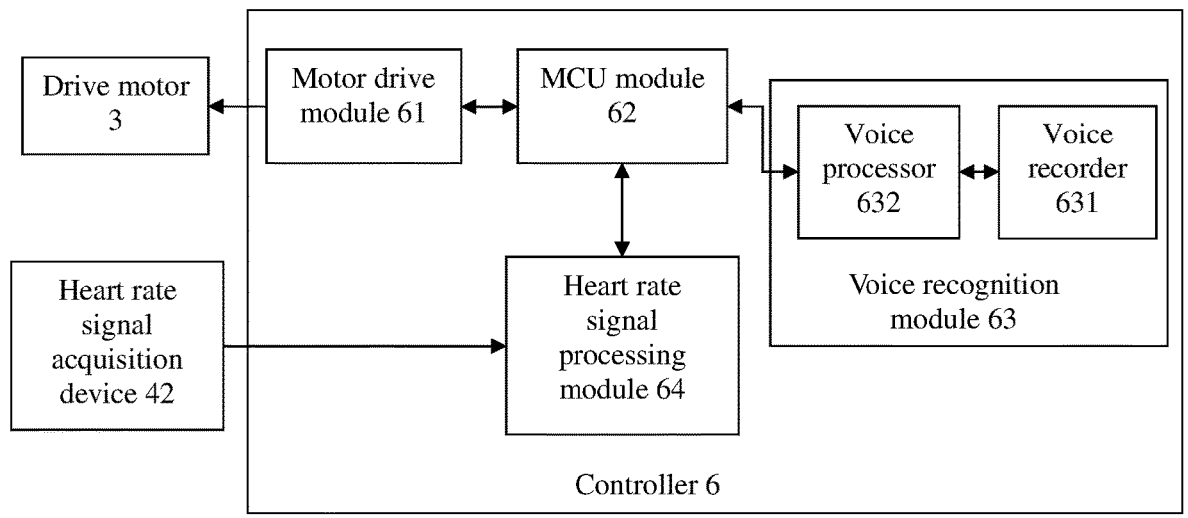
FIG. 3 is a structure and connection diagram of a controller in an embodiment of the present invention.
Figure 4:
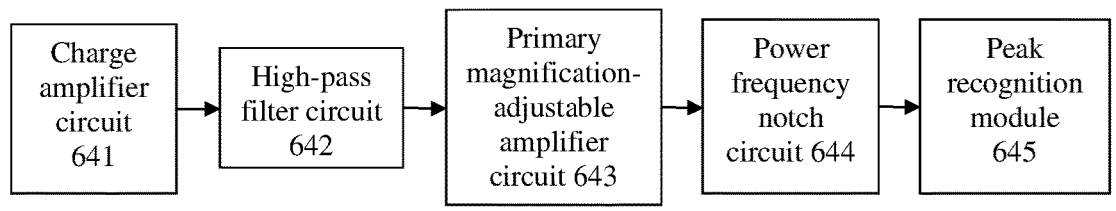
FIG. 4 is a structure diagram of a heart rate signal processing module in an embodiment of the present invention.

The technical solution of the present invention will be described below in detail through drawings and a specific embodiment. It is to be understood that the embodiment of the present invention and specific technical characteristics in the embodiment are descriptions of the technical solution of the prevent invention only rather than limitations. The embodiment of the present invention may be combined with the specific technical characteristics in the embodiment under the circumstance that no conflict occurs.

As shown in FIG. 1, FIG. 2, FIG. 3 and FIG. 4, a nursing bed based on heart rate monitoring and voice recognition includes a nursing bed body, a drive motor 3 and a controller 6.

The nursing bed body includes a bed body fixed part 2, a bed body movable part 1 and a connector 5. The bed body fixed part 2 is hinged with a side of the connector 5, and the bed body moveable part 1 is connected with another side of the connector 5 fixedly.

A motor base of the drive motor 3 is installed on the bed body fixed part 2 fixedly, an output shaft of the drive motor 3 is connected with another part of the connector 5 in a meshing manner, and the drive motor 3 is configured to drive the bed body moveable part 1 to swing through the connector 5.

The controller 6 is installed on the nursing bed body and electrically connected with the drive motor 3. The controller 6 includes a motor drive module 61, an MCU module 62 and a voice recognition module 63. The voice recognition module 63 is configured to acquire voice information of a user and send the voice information to the MCU module 62. The MCU module 62 is configured to analyze the voice information that is received and generate a control instruction of controlling the motor drive module 61. The motor drive module 61 is configured to receive the control instruction of the MCU module 62, and accordingly control operations of the drive motor 3.

Figure 5:
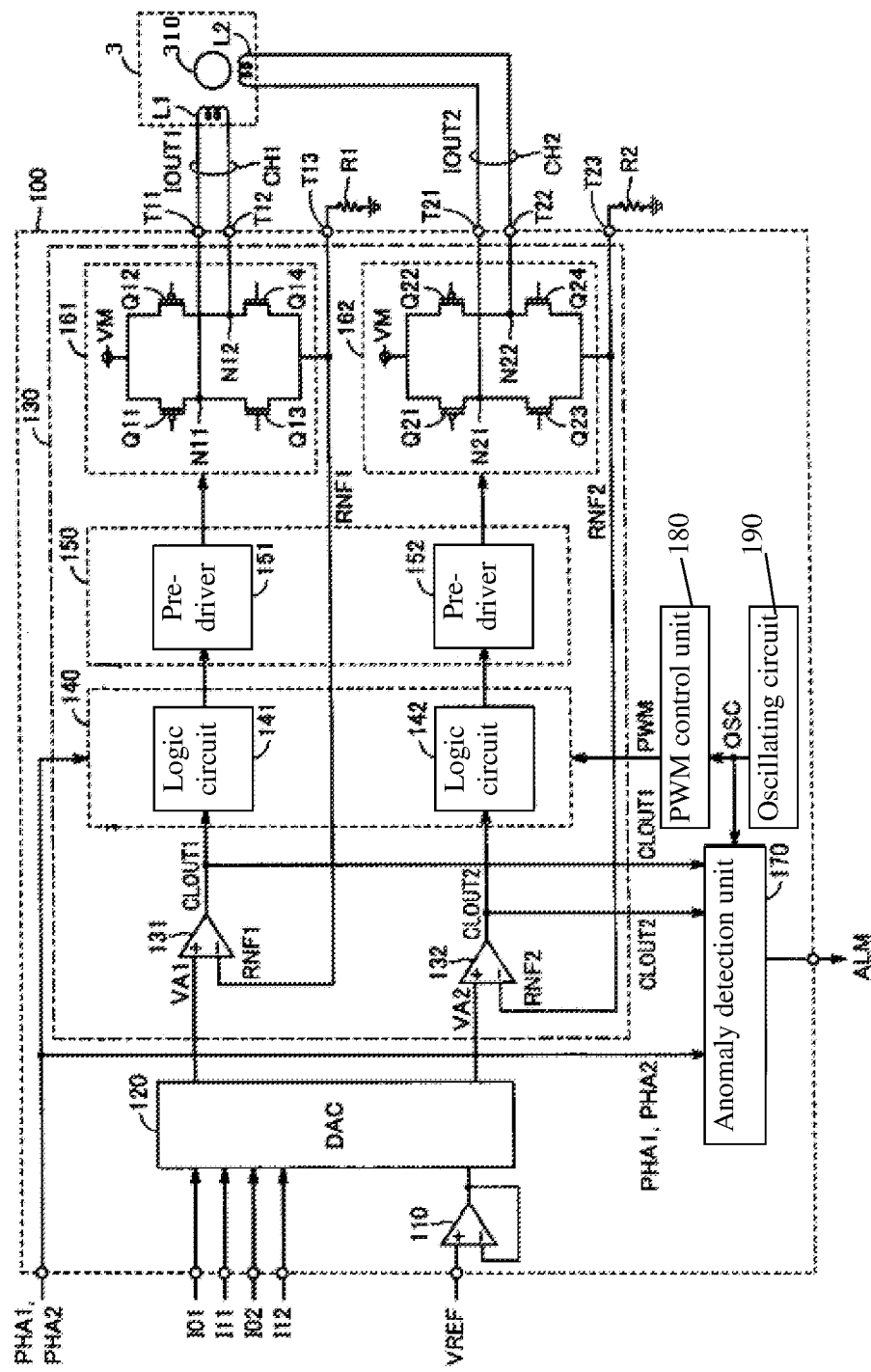
FIG. 5 is a structure diagram of a motor drive module in an embodiment of the present invention.

Further, in the embodiment of the present invention, as shown in FIG. 5, the motor drive module includes: the drive motor 3 is a stepping motor 3 specifically. The stepping motor 3 is a two-phase stepping motor and includes exciting coils L1 and L2 which respectively correspond to two phases and a rotor 310.

Exciting currents IOUT1 and IOUT2 flow through the exciting coils L1 and L2, respectively. A drive circuit 100 controls the exciting currents IOUT1 and IOUT2, to keep values of the exciting currents IOUT1 and IOUT2 as setting values when driving the stepping motor 3.

Moreover, in the embodiment, assume that the stepping motor is driven by the drive circuit 100 in a microstepping manner, namely the drive motor 100 drives the rotor 310 of the stepping motor to rotate with a stepping angle which is subtler than a basic stepping angle through subtly changing a ratio of the exciting currents IOUT1 and IOUT2.

The drive circuit 100 includes an input buffer 110, a D/A converter (DAC) 120, a current control circuit 130, an anomaly detection unit 170, a PWM control unit 180 and an oscillating circuit 190.

The current control circuit 130 includes comparators 131 and 132, a logic control unit 140 having logic circuits 141 and 142, a pre-driver unit 150 having pre-drivers 151 and 152, and H bridges 161 and 162.

Through the comparator 131, the logic circuit 141, the pre-driver 151 and the H bridge 161, a circuit corresponding to a channel CH1 for supplying the exciting current IOUT1 to the exciting coil 1 is formed. Moreover, through the comparator 132, the logic circuit 142, the pre-driver 152 and the H bridge 162, the circuit corresponding to a channel CH2 for supplying the exciting current IOUT2 to the exciting coil 2 is formed. The circuits which respectively correspond to the channels CH1 and CH2 have identical structure and functions, therefore the channel CH1 will be described in the detailed description of the circuit which is shown below, while the channel CH2 will not be described repeatedly and identically.

The input buffer 110 is a so-called voltage follower circuit which is configured to output an input reference voltage VREF. The reference voltage VREF is a voltage indicating upper limits of the exciting current IOUT1 and IOUT2.

The DAC 120 corresponds to 'A target voltage generating unit' in the drive circuit of the stepping motor of the present invention. The DAC 120 receives the reference voltage VREF and control signals I01 and I11 and outputs a target voltage VA1 relative to the channel CH1. Moreover, the control signals I01 and I11 are the signals which make a ratio of the setting value of the exciting current IOUT1 to the upper limit of the exciting current IOUT1 change between 0 and 1.

Further, in the embodiment of the present invention, the connector 5 is a connecting shaft whose one end is equipped with an input gear. One side of the bed body fixed part 2 is provided with multiple hinge rings. The connector 5 is sleeved into the hinge rings. One side of the bed body moveable part 1 is welded on the connector 5. A motor shaft of the drive motor 3 is equipped with an output gear, and the output gear on the motor shaft of the drive motor 3 is meshed with the input gear on the connector 5.

Further, in the embodiment of the present invention, the nursing bed based on heart rate monitoring and voice recognition further includes a heart rate testing mattress. The heart rate testing mattress includes a mattress main body 41 and a heart rate signal acquisition device 42. The controller 6 further includes a heart rate signal processing module 64. The heart rate signal acquisition device 42 is arranged under the mattress main body 41 and configured to acquire a vibration signal of the mattress and transmit the vibration signal to the heart rate signal processing module 64. The heart rate signal processing module 64 is configured to sample, quantify and filter the vibration signal, so as to acquire a heart rate vibration signal, and transmit the heart rate vibration signal to the MCU module 62. The MCU module 62 is further configured to analyze the heart rate vibration signal that is received, to accordingly analyze a sleep state and/or health state of a person on the heart rate testing mattress.

Preferably, the heart rate signal acquisition device 42 is a piezoelectric film sensor or an ECG sensor strip or a gasket.

Preferably, the heart rate signal acquisition device 42 is arranged in an interlayer of the mattress main body 41 and confirms a heart rate of a patient through an acquired electric signal. In one embodiment, the electric signal is acquired by arranging a series of ECG sensor strips or gaskets in a central part of the mattress along a surface of the interlayer of the mattress main body 41, and the ECG sensor strips or gaskets are positioned in the central part and extract ECG signals from the patient. The heart rate signal acquisition device 42 is connected with the heart rate signal processing module 64. The heart rate signal processing module 64 includes a heart rate integrated processor and a storage device, or may communicate with the independent MCU module 62. Under any condition, the storage device may load an algorithm of calculating the heart rate of the user on the basis of ECG signals acquired from the ECG sensor strips or gaskets. For example, the algorithm may be configured to calculate the heart rate of the user with an R wave interval which is calculated by the ECG sensor strips or gaskets, or the algorithm may select two ECG signals received from the ECG sensor strips or gaskets and measure a heart dipole between two leads, as differential measurement.

Further, in the embodiment of the present invention, the heart rate signal processing module 64 is connected with the heart rate signal acquisition device 42 to process the electric signal and accordingly acquire a second electric signal. The heart rate signal processing module 64 includes a charge amplifier circuit 641, a high-pass filter circuit 642, a primary magnification-adjustable amplifier circuit 643, a 50 Hz power frequency notch circuit 644 and a peak recognition module 645 which are connected sequentially. The heart rate signal processing module 64 may output a ±12V analog electric signal. Signal intensity of the ±12V analog electric signal may clearly reflect tiny changes of heartbeats and undulant breathing of the human body on the heart rate signal acquisition device 42 which is connected with the heart rate signal processing module 64. The capacitive-feedback-type charge amplifier circuit 641 which is formed by an operational amplifier and corresponding resistor and capacitor elements is connected with the heart rate signal acquisition device 42, to convert a current signal into a voltage signal. The high-pass filter circuit 642 is configured to filter the voltage signal and prevent the signal of less than 0.01 Hz. The primary magnification-adjustable amplifier circuit 643 is designed with an AD620 chip, to amplify the voltage signal after filtering. The mentioned three circuits may eliminate influence of baseline drift while filtering undesired signals, amplifying a tiny heart impulse signal and the undulant breathing signal until they meet requirements of A/D conversion. Finally, the 50 Hz power frequency notch circuit 644 which is formed by UAF42 in combination with corresponding resistor network is taken to eliminate a 50 Hz frequency component in the voltage signal, so as to acquire the second voltage signal and accordingly restrain power frequency interference caused during measurement of the heart rate signal acquisition device 42. The heart rate signal processing module 64 extracts a heart impulse signal from the vibration signal through amplitude constraints and time constraints, then the peak recognition module 645 acquires a stroke volume and an impulse interval of the heart in accordance with a peak of the heart impulse signal and time corresponding to the peak and finally calculates the heart rate, heat rate variability and pressure relaxation index based on ballistocardiography (BCG) principle.

Further, in the embodiment of the present invention, the MCU module 62 checks whether the heart rate and/or breathing rate analyzed by the heart rate signal processing module 64 falls into an interval value and accordingly judges whether the user on the mattress falls asleep. The MCU module 62 adjusts an angle of the bed body fixed part 2 and the bed body moveable part 1 in accordance with a predetermined setting mode.

Further, in the embodiment of the present invention, the voice recognition module 63 includes a voice recorder 631 and a voice processor 632. The voice processor 632 includes a voice recognition instruction library unit, a voice input unit, an analysis morpheme unit and an instruction reference unit. The voice recorder 631 is configured to record and generate voice information.

The voice input unit is configured to pre-process the voice information generated by the voice recorder 631. The analysis morpheme unit is configured to store the voice information after pre-processing and analyze various morpheme information or character strings. The instruction reference unit collates phrases for various morpheme information or character strings while generating the control instruction and sending the control instruction to the MCU module 62.

Further, in the embodiment of the present invention, a voice library is provided with a plurality of instruction groups and each including a primary voice instruction and a secondary voice instruction group. One primary voice instruction corresponds to one secondary voice instruction group, and each secondary voice instruction group is provided with a plurality of secondary voice instructions. The primary voice instruction is a group name of the instruction group, and each voice instruction in the secondary voice instruction group is an operating instruction of corresponding equipment. A server end includes one voice library in which the user is allowed to edit and set each instruction group. Each secondary voice instruction has corresponding equipment operations. Each voice instruction in the voice library is provided with voice feedback information. The voice feedback information is a voice prompt message which is implemented after operations of the voice instruction. A voice recognition terminal is provided with a voice recognition engine and a voice command stack. The voice recognition engine is configured to gather voice sent by the user while converting the voice into character or Pinyin-type or phonetic wave type voice instruction. The voice command stack is provided with an instruction space which is configured to store an instruction set sent from the server end. The instruction set is characterized in that the voice instruction inquires in the voice library of the server end to acquire all corresponding secondary voice instruction groups under the primary voice instruction and the primary voice instruction. The user may select certain primary and secondary voice instructions of controlling the operating equipment by inquiring all acquired secondary voice instructions, and implement corresponding operations for the corresponding equipment through the server end in accordance with the secondary voice instruction.

Further, in the embodiment of the present invention, various morpheme information or character strings exist in form of code.

Further, in the embodiment of the present invention, the instruction reference unit includes a weight database, a translation thesaurus and a response matching database based on AIML language. The weight database is configured to store a weight of a combination way of each lemma in literal information.

Further, in the embodiment of the present invention, the voice recorder 631 includes a microphone, a noise reduction device and a voice chip which are connected sequentially.

The voice chip is connected with the voice processor 632. The voice chip is configured to implement digital-to-analog conversion for voice that is received and generate the voice information. The noise reduction device is configured to implement noise reduction for the voice information received from the microphone.

Preferably, the voice chip is PM66.

Further, in the embodiment of the present invention, the voice processor 632 uses the voice recognition engine Sphinx-4. A recognition principle framework of the voice recognition engine Sphinx-4 mainly includes a voice front-end service module, a language analysis module and a language decoding module. The voice front-end service module consists of one or more parallel processors of processing a calculating signal, and is configured to extract one or more voice signals therein in accordance with the input voice information and convert their parameters into a series of characteristic sequences, for input of the language decoding module. The language analysis module acquires a searching path which is used by the language decoding module in combination with a method described in a voice model, pronunciation in a pronouncing dictionary and characteristic parameters of an acoustic model. The language decoding module generates a final recognition result with the language analysis module on the basis of the characteristic sequence acquired by the voice front-end service module and output the final recognition result.

Further, in the embodiment of the present invention, the controller 6 further includes a communication module. The communication module is configured to communicate with the Internet or a wireless network outside the nursing bed based on heart rate monitoring and voice recognition.

Further, in the embodiment of the present invention, the communication module communicates with a cloud server in the Internet or the wireless network.

Preferably, the communication module is a 4G communication module and/or a WIFI wireless communication module.

Further, in the embodiment of the present invention, the nursing bed based on heart rate monitoring and voice recognition further includes a monitoring module. The monitoring module is installed on the bed body fixed part 2 or the bed body moveable part 1 and configured to acquire video data and transmit the video data to the communication module.

Further, in the embodiment of the present invention, the monitoring module further transmits the video data to the cloud server, in this way the cloud server transmits the video data to a remote monitoring terminal in the Internet or the wireless network.

Further, in the embodiment of the present invention, the nursing bed based on heart rate monitoring and voice recognition further includes a positioning module. The positioning module is configured to acquire positioning information of the nursing bed based on heart rate monitoring and voice recognition and transmit the positioning information to the communication module.

Further, in the embodiment of the present invention, the nursing bed based on heart rate monitoring and voice recognition further includes a vital sign sensor. The vital sign sensor is arranged on the bed body fixed part 2 or the bed body moveable part 1 and configured to acquire physiological characteristic data of the user and transmit the physiological characteristic data to the communication module.

Further, in the embodiment of the present invention, the vital sign sensor sends the physiological characteristic data to the cloud server in the Internet or the wireless network.

Further, in the embodiment of the present invention, the nursing bed based on heart rate monitoring and voice recognition further includes a voice output module. The voice output module is arranged on the bed body fixed part 2 or the bed body moveable part 1 and configured to acquire voice data and transmit the voice data to the communication module.

Further, in the embodiment of the present invention, the voice output module is connected with the cloud server through the communication module, to output the voice data sent from the cloud server in the Internet or the wireless network.

Further, in the embodiment of the present invention, the nursing bed based on heart rate monitoring and voice recognition further includes an image acquisition device. The image acquisition device is arranged on the bed body fixed part 2 or the bed body moveable part 1 and configured to acquire image data or video data and transmit the image data or video data to the communication module.

Further, in the embodiment of the present invention, the image acquisition device transmits the acquired image data or video data to the cloud server through the communication module.

Although the example embodiment of the application is described, those of ordinary skill in the art may make other changes and modifications of these embodiments upon knowing the basic creative concept. Therefore, it is intended that the attached claims are explained to include the example embodiment and all changes and modifications falling into the scope of the application, including changing ways of determining the peak with a specific symbol and a specific sign.

It is apparent that various modifications and variations of the application may be made by those skilled in the art without departing from the spirit and scope of the application. In this way, the application is further intended to include these modifications and variations if these modifications and variations of the application belong to the scope of the claims of the application and the equivalent technology thereof.

What is claimed is:

1. A nursing bed based on heart rate monitoring and voice recognition, wherein the nursing bed based on heart rate monitoring and voice recognition comprises a nursing bed body, a drive motor and a controller;

the nursing bed body comprises a bed body fixed part, a bed body movable part and a connector; the bed body fixed part is hinged with a side of the connector, and the bed body moveable part is connected with another side of the connector fixedly;

a motor base of the drive motor is installed on the bed body fixed part fixedly, an output shaft of the drive motor is connected with another part of the connector in a meshing manner, and the drive motor is configured to drive the bed body moveable part to swing through the connector;

the controller comprises a motor drive module, a microcontroller unit (MCU) and a voice recognition module; the voice recognition module is configured to acquire voice information of a user and send the voice information to the MCU; the MCU is configured to analyze the voice information that is received and generate a control instruction of controlling the motor drive module; the motor drive module is configured to receive the control instruction of the MCU, and accordingly control operations of the drive motor;

the nursing bed based on heart rate monitoring and voice recognition further comprises a heart rate testing mattress; the heart rate testing mattress comprises a mattress main body and a heart rate signal acquisition device; the controller further comprises a heart rate signal processor; the heart rate signal acquisition device is arranged under the mattress main body and configured to acquire a signal and transmit the signal to the heart rate signal processor; the heart rate signal processor is configured to sample, quantify and filter the signal, so as to acquire a heart rate, and transmit a heart rate signal carrying the heart rate to the MCU; and the MCU is further configured to analyze the heart rate signal that is received, to check whether the heart rate falls into an interval value and adjust an angle of the bed body fixed part and the bed body moveable part in accordance with a predetermined setting mode;

the heart rate signal processor comprises a capacitive-feedback-type charge amplifier circuit, a high-pass filter circuit, a primary magnification-adjustable amplifier circuit, a 50 Hz power frequency notch circuit and a peak recognition module which are connected sequentially;

the heart rate signal acquisition device comprises a series of ECG sensor strips or gaskets positioned in a central part of the mattress along a surface of an interlayer of the mattress main body, and is configured to acquire a current signal representing the heart rate;

the capacitive-feedback-type charge amplifier circuit, formed by an operational amplifier and corresponding resistor and capacitor elements, is connected with the heart rate signal acquisition device, and is configured to convert the current signal into a voltage signal;

the high-pass filter circuit is configured to filter the voltage signal and prevent the signal of less than 0.01 Hz to output a voltage signal after filtering; the primary magnification-adjustable amplifier circuit is designed with an AD620 chip, and is configured to amplify the voltage signal after filtering;

the 50 Hz power frequency notch circuit is formed by a UAF42 chip in combination with corresponding resistor network, and is configured to eliminate a 50 Hz frequency component in the amplified voltage signal after filtering so as to acquire a second voltage signal representing a heart impulse signal; and the peak recognition module is configured to acquire a stroke volume and an impulse interval of the heart in accordance with a peak of the heart impulse signal and time corresponding to the peak and calculate the heart rate with an R wave interval which is calculated by the ECG sensor strips or gaskets, or by selecting two ECG signals received from the ECG sensor strips or gaskets and measuring a heart dipole between two leads, as differential measurement.

2. The nursing bed based on heart rate monitoring and voice recognition as claimed in claim 1, wherein the voice recognition module comprises a voice recorder and a voice processor; the voice recorder is configured to record and generate voice information;

the voice processor is configured to pre-process the voice information generated by the voice recorder, store the voice information after pre-processing and analyze various morpheme information or character strings, and collate phrases for various morpheme information or character strings while generating the control instruction and sending the control instruction to the MCU.

3. The nursing bed based on heart rate monitoring and voice recognition as claimed in claim 1, wherein the voice recorder comprises a microphone, a noise reduction device and a voice chip which are connected sequentially;

the voice chip is connected with the voice processor; the voice chip is configured to implement digital-to-analog conversion for voice that is received and generate the voice information; and the noise reduction device is configured to implement noise reduction for the voice information received from the microphone.

4. The nursing bed based on heart rate monitoring and voice recognition as claimed in claim 1, wherein the controller is further configured to communicate with the Internet or a wireless network outside the nursing bed based on heart rate monitoring and voice recognition.

5. The nursing bed based on heart rate monitoring and voice recognition as claimed in claim 4, wherein the nursing bed based on heart rate monitoring and voice recognition further comprises a voice output device; and the voice output device is arranged on the bed body fixed part or the bed body moveable part and configured to acquire voice data and transmit the voice data to the controller.

* * * * *